United States Patent [19]

Bianchi

[11] Patent Number: 5,714,325
[45] Date of Patent: Feb. 3, 1998

[54] PRENATAL DIAGNOSIS BY ISOLATION OF FETAL GRANULOCYTES FROM MATERNAL BLOOD

[75] Inventor: Diana W. Bianchi, Brookline, Mass.

[73] Assignee: New England Medical Center Hospitals, Boston, Mass.

[21] Appl. No.: 127,257

[22] Filed: Sep. 24, 1993

[51] Int. Cl.$^6$ .................. C12Q 1/68; G01N 33/53; C07K 16/28
[52] U.S. Cl. .................. 435/6; 435/40.5; 435/7.21; 435/7.24; 435/7.25; 436/519; 436/520; 436/63; 530/388.7; 530/389.6; 935/77; 935/78
[58] Field of Search .................. 435/6, 91.2, 7.24, 435/7.21, 7.25, 40.5; 536/25.4; 436/63, 519, 520, 524; 530/389.6, 388.7; 935/77, 78

[56] References Cited

FOREIGN PATENT DOCUMENTS

WO 91/07660  11/1990  WIPO.
   9107660   5/1991  WIPO.

OTHER PUBLICATIONS

Elias et al., "First trimester prenatal diagnosis of trisomy 21 in fetal cells from maternal blood" *The Lancet: Letters to the Editor*, vol. 340, p. 1033, Oct. 24, 1992.
Grozdea et al., "Cytochemical and biochemical studies on neutrophil alkaline phosphatase in parents of trisomy 21 children" *Human Genetics*, vol. 67, pp. 313–316, 1984.
Schröder et al., "Fetal Leukocytes in the Maternal Circulation After Delivery" *Transplantation*, vol. 17, No. 4, pp. 346–354, Apr. 1974.
Wessman et al., "Fetal Granulocytes in Maternal Venous Blood Detected by in situ Hybridization" *Prenatal Diagnosis*, vol. 12, pp. 993–1000, 1992.
Wachtel et al Human Reproduction (1991) 6:1466–1469.
Bianchi et al Proc Natl Acad Sci, USA (1990) 87:3279–3283.
Wessman et al Prenatal Diagnosis (1992, Dec). 12:993–1000.
Cullen et al Biochemical Medicine (1980) 23: 133–143.
Brison et al, Molec & Cellular Biology (1982) 2: 578–587.
Bianchi et al, Prenatal Diagnosis (Apr. 1993) 13: 293–300.
Klinger et al Am J Hum Genetics (1992) 51:55–65.

*Primary Examiner*—Carla J. Myers
*Attorney, Agent, or Firm*—Elizabeth A. Hanley; Lahive & Cockfield

[57] ABSTRACT

A method for detecting presence or absence of a nucleic acid of interest in fetal nucleic acid derived from a sample of peripheral blood obtained from a pregnant woman is described. The method involves obtaining a sample of peripheral blood from a pregnant woman, treating the sample of peripheral blood such that fetal nucleic acid present in fetal granulocytes is made available for detection and detecting presence or absence of a nucleic acid of interest in the available fetal nucleic acid. The proportion of fetal granulocytes present in the sample of peripheral blood can be increased relative to the sample of peripheral blood forming a sample enriched in fetal granulocytes prior to the detection step. The nucleic acid of interest can be detected by treating the peripheral blood sample such that fetal granulocyte nucleic acid present in the sample is made available for hybridization with a nucleic acid probe and subsequently contacting the available fetal nucleic acid with a nucleic acid probe hybridizable to a nucleic acid of interest under hybridization conditions. The presence or absence of hybridization between the nucleic acid probe and the nucleic acid of interest is detected as an indication of the presence or absence of the nucleic acid of interest in the fetal nucleic acid.

19 Claims, 5 Drawing Sheets

PRENATAL DIAGNOSIS BY ISOLATION OF FETAL GRANULOCYTES FROM MATERNAL BLOOD

BACKGROUND OF THE INVENTION

Granulocytes are one subpopulation of white blood cells found in the blood. There are three types or subsets of granulocytes (which collectively are also referred to as polymorphonuclear leukocytes): neutrophils, basophils and eosinophils. All granulocytes have a distinctive morphology characterized by a tri-lobed nucleus and abundant cellular granules. The three subsets can be distinguished by their differing affinities for certain dyes. Granulocytes are known to migrate to infected areas and play a major functional role in inflammatory responses. In adults, granulocytes are continually produced in the bone marrow, are released into the circulation and then migrate to tissues. The lifespan of granulocytes once released from the bone marrow is normally 4 to 8 hours in the circulation and another 4 to 5 days in the tissues.

During pregnancy, a variety of cell types of fetal origin cross the placenta and circulate within maternal peripheral blood. For a review see Bianchi, D. W. and Klinger, K. W. in *Genetic Disorders and the Fetus: Prevention and Treatment*, 3rd edition, Baltimore/London: The John Hopkins University Press (1992). These cells are a potential source of information about the gender and genetic makeup of the developing fetus. The feasability of using fetal cells in the maternal circulation for diagnostic purposes, however, is greatly hindered by the fact that fetal cells are present in maternal blood in only very limited numbers. In addition, most fetal cells (with the exception of trophoblasts) cannot be distinguished from maternal cells on the basis of morphology alone, but rather must be identified based upon detection of fetal cell markers or fetal DNA. Detection of fetal cells in maternal blood can be improved by enrichment for fetal cells within the mixture of fetal and maternal cells and/or by separation of fetal cells from maternal cells. One approach that has been used to achieve enrichment for and separation of fetal cells within a maternal blood sample utilizes antibodies specific for a particular fetal cell type to label fetal cells. For example, fetal-specific antibodies can be used to label fetal cells in order to facilitate separation of these cells from maternal components by flow cytometry. Herzenberg, L. A., et al., *Proc. Natl. Acad. Sci. USA* 76, 1453–1455 (1979); Iverson, G. M., et al., *Prenatal Diagnosis* 1, 61–73 (1981); Bianchi, D. W., et al., *Prenatal Diagnosis* 11, 523–528 (1991). One particular fetal cell type within maternal blood that has been demonstrated to be useful for detecting fetal DNA is the nucleated erythrocyte. Bianchi, D. W., et al. *Proc. Natl. Acad Sci. USA* 87, 3279–3283 (1990); Bianchi, D. W. et al., *Hum. Genet.* 90, 368–370 (1992): Bianchi, D. W. et al., *Prenatal Diagnosis* 13, 293–300 (1993); PCT Publication WO 91/07660.

Fetal granulocytes have been reported to be present in maternal blood. Zilliacus, R., et al. *Scand. J. Haematol.* 15, 33–338 (1975); Siebers, J. W., et al. *Humangenetik* 28, 273–280 (1975); Wessman, M., et al. *Prenatal Diagnosis* 12, 993–1000 (1992). However, the prevalence of fetal granulocytes in maternal blood reported in these studies varies markedly between the studies, and the method used to identify fetal cells in two of the studies (Zilliacus, R., et al. *Scand. J. Haematol.* 15, 33–338 (1975); Siebers, J. W., et al. *Humangenetik* 28, 273–280 (1975)), by counting Y-bodies, is not considered to be a reliable indicator of fetal cells. Fetal granulocytes were not enriched for in any of these studies, which necessitated examination of many thousands of cells within a maternal blood sample in order to detect a very rare potential fetal cell. While Wessman et al. (*Prenatal Diagnosis* 12, 993–1000 (1992)) were able to detect fetal Y chromosomal DNA by in situ hybridization of unenriched fetal granulocytes in maternal blood, it is unclear, given the extreme rarity of these cells in maternal blood, that this result could be reproduced reliably.

SUMMARY OF THE INVENTION

The present invention is based, at least in part, on the discovery that fetal granulocytes are present in the peripheral blood of a pregnant woman at a level which allows them to be useful in prenatal diagnostic methods. The invention is further based, at least in part, on the discovery that fetal granulocytes can be separated from maternal cells within a maternal blood sample. The invention is still further based, at least in part, on the discovery that fetal nucleic acid in fetal granulocytes from a maternal blood sample can be detected. The method of the present invention is non-invasive because a peripheral blood sample from a pregnant woman, not fetal blood, is used as the source of the fetal nucleic acid. Fetal nucleic acid is derived from fetal granulocytes present in the peripheral blood of a pregnant woman. The method of the present invention can be used to assess fetal characteristics (e.g. fetal sex and chromosomal abnormalities) or can be used to diagnose whether a fetus has a prenatal disease at an early stage of the gestational period. The non-invasive method of the present invention does not expose the fetus or mother to risks, e.g. infection, fetal injury, and miscarriage, associated with invasive methods such as amniocentesis. Additionally, given the short lifespan of granulocytes, detection of fetal granulocytes in maternal blood preferentially detects fetal cells of a current pregnancy rather than fetal cells which may persist from a former pregnancy.

The present invention pertains to a method of detecting the presence or absence of a nucleic acid of interest in fetal nucleic acid derived from fetal granulocytes within a sample of peripheral blood obtained from a pregnant woman. The method involves obtaining a sample of peripheral blood from a pregnant woman, treating the sample of peripheral blood such that fetal nucleic acid present in fetal granulocytes is made available for detection and detecting the presence or absence of the nucleic acid of interest in the available fetal nucleic acid.

The proportion of fetal granulocytes present in the sample of peripheral blood can be increased relative to the starting sample, forming a sample enriched in fetal granulocytes prior to detecting fetal nucleic acid. The proportion of fetal granulocytes can be increased by separating nucleated cells from non-nucleated cells in the sample of peripheral blood to form a nucleated cell enriched sample. The proportion of fetal granulocytes can be further increased by treating the nucleated cell enriched sample such that fetal granulocytes can be separated from the nucleated cell enriched sample to form a fetal granulocyte enriched sample.

A nucleic acid of interest can be detected by treating the fetal granulocyte enriched sample such that fetal nucleic acid present in the sample is made available for hybridization with a nucleic acid probe and subsequently contacting the available fetal nucleic acid with a nucleic acid probe hybridizable to the nucleic acid of interest under hybridization conditions. The presence or absence of hybridization between the nucleic acid probe and the nucleic acid of interest is detected as an indication of the presence or absence of the nucleic acid of interest in the fetal nucleic acid.

The method of the present invention can be used to determine the sex of a fetus by contacting DNA of fetal granulocytes derived from a sample of peripheral blood from a woman pregnant with a fetus with a nucleic acid probe hybridizable to Y chromosomal DNA. The presence of hybridization between the nucleic acid probe and Y chromosomal DNA in fetal DNA is detected as an indication of a male fetus or the absence of hybridization is detected as an indication of a female fetus.

The method of the present invention also can be used for diagnosing a disease in a fetus. The nucleic acid of fetal granulocytes derived from a sample of peripheral blood obtained from a woman pregnant with a fetus is contacted with a nucleic acid probe hybridizable to a nucleic acid of interest associated with a disease under hybridization conditions. The presence of a hybridization pattern associated with the disease between the nucleic acid probe and the nucleic acid of interest in fetal nucleic acid is detected as an indication of whether or not the fetus has the disease.

The method of the present invention also can be used to detect a chromosomal abnormality in a fetus such as a chromosomal aneuploidy, e.g., trisomy 13, trisomy 18, or trisomy 21. A sample of peripheral blood from a woman pregnant with a fetus is obtained. The fetal granulocytes are separated from the peripheral blood sample onto a solid support forming immobilized fetal granulocyte material, e.g. metaphase or interphase nuclei. The immobilized fetal granulocyte material is contacted with a nucleic acid probe hybridizable to chromosomal DNA of interest under hybridization conditions. A difference in hybridization of the nucleic acid probe to chromosomal DNA of interest from fetal granulocytes as compared to hybridization of the probe to chromosomal DNA from normal cell is detected as an indication of the presence of a chromosomal abnormality in the fetal chromosomal DNA.

Other aspects of this invention relate to methods of enriching the peripheral maternal blood sample and kits containing reagents used to conduct the described methods. These aspects are described in more detail below.

DETAILED DESCRIPTION OF THE INVENTION

Figure 1:
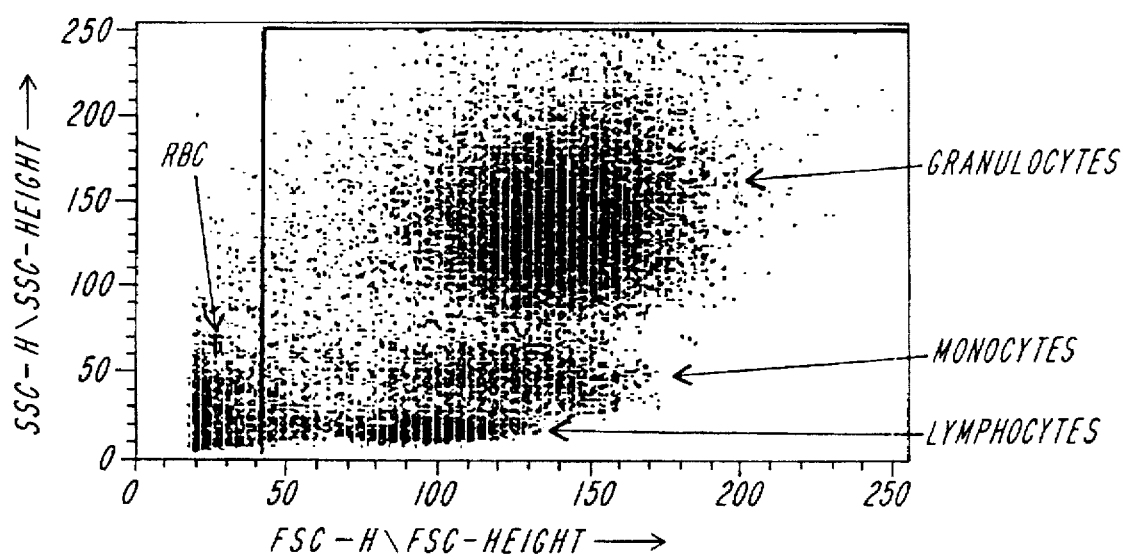
FIG. 1 is a flow cytometric graph depicting the scatter profile of cells present in a nucleated cell enriched sample derived from a maternal blood sample. Forward angle light scatter is on the X axis and side scatter is on the Y axis.

The present invention relates to an in vitro method of enriching for and separating fetal granulocytes present in a sample of peripheral blood obtained from a pregnant woman (a maternal blood sample) and of enriching for and separating fetal nucleic acid from maternal nucleic acid. It further relates to an in vitro method of prenatal detection and/or quantitation of selected fetal nucleic acid in nucleic acid isolated from the maternal blood sample. The method provides a noninvasive approach to detect and/or quantitate a nucleic acid of interest, such as that associated with a disease or a condition whose assessment during gestation is desired, in fetal nucleic acid. It also provides a noninvasive means by which the sex of a fetus can be determined. Because of the short lifespan of granulocytes, analysis of fetal granulocyte nucleic acid provides information about a current fetus, thereby avoiding the possibility that the fetal cells detected in maternal blood may be from a former pregnancy.

In the present method, fetal granulocytes are enriched for and separated from a maternal peripheral blood sample by means of a detectable material which binds to the fetal granulocytes but not to maternal cells and which facilitates separation of granulocytes from the maternal sample. A population of completely pure, isolated fetal granulocytes may not necessarily be achieved by this method, but what is important is that the cell sample which is produced by use of this method is one in which the proportion of fetal granulocytes present in the sample is greatly increased compared to the proportion of fetal granulocytes present in the original blood sample obtained from the pregnant woman. Thus, the resultant cell sample is one which is highly enriched in fetal granulocytes. This enrichment for fetal granulocytes is sufficient to allow for detection of fetal nucleic acid in the fetal granulocytes which otherwise could not be detected in the unenriched, original blood sample. The fetal granulocytes in the enriched cell sample can include both mature, differentiated granulocytes and immature granulocyte precursors. In one embodiment of the present method, at least one detectably labelled monoclonal antibody which binds to an antigen present on fetal granulocytes but not on maternal cells is combined with a maternal blood sample and, once bound to fetal granulocytes, facilitates separation of fetal granulocytes from the maternal sample. In another embodiment, at least one detectably labelled monoclonal antibody which binds to an antigen present on maternal cells but not on fetal granulocytes is used to remove maternal cells from the maternal blood sample to thereby enrich for fetal granulocytes. In a further embodiment, two different monoclonal antibodies which bind to antigens present on fetal granulocytes but not on maternal cells are used in combination to separate fetal granulocytes from maternal blood thereby enriching for fetal granulocytes.

In the case in which the detectable label is a fluorescent molecule, separation can be carried out by means of flow cytometry, in which fluorescently-labelled molecules are separated from unlabelled molecules. This results in separation of fetal granulocytes from maternal cells and thus of fetal nucleic acid from maternal nucleic acid. That this separation has occurred can be verified using known techniques, such as microscopy and detection of fetal cell markers.

In one embodiment of the method of the present invention by which the presence of a selected nucleic acid of interest in fetal nucleic acid is determined (detected and/or quantitated), the isolated fetal granulocytes are treated to render nucleic acid present in them available for amplification. Amplification of fetal nucleic acid, e.g. DNA, from fetal granulocytes is carried out using a known amplification technique, such as the polymerase chain reaction (PCR). Amplified fetal granulocyte DNA can be subsequently separated on the basis of size (e.g. by gel electrophoresis) and contacted with a selected labelled probe, such as labelled nucleic acid complementary to a nucleic acid of interest (e.g. complementary to an abnormal gene or gene portion, or Y-specific DNA). Detection of the labelled probe after it has hybridized to fetal DNA results in detection of the sequence of interest in the fetal DNA. Quantitation of the hybridized labelled probe results in quantitation of the fetal DNA.

Another embodiment of the invention is a method for assessing chromosomal abnormalities in a fetus. Cells isolated as described above are separated onto a solid support, such as a slide, and screened for chromosomal abnormalities using in situ hybridization. In this embodiment, a selected nucleic acid probe, such as a labelled DNA probe for chromosomal DNA associated with a chromosomal abnormality, is combined with fetal granulocyte DNA under conditions appropriate for hybridization of complementary sequences to occur. Detection and/or quantitation of the labelled probe after hybridization results in detection and/or quantitation of the fetal DNA to which the probe has hybridized. A difference or differences in the hybridization of the labelled DNA probe to fetal DNA as compared to hybridization of the labelled DNA probe to DNA from a normal cell (i.e. a cell which does not have a chromosomal abnormality in the DNA of interest) can be detected as an indication of the presence of a chromosomal abnormality in the fetal DNA. For example, a trisomy in the fetal DNA can be detected by hybridization of a labelled DNA probe to three chromosomes in the fetal DNA as compared to hybridization to only two chromosomes in normal cells.

Another embodiment of the invention is a method for determining the sex of a fetus. Cells isolated as described above and separated onto a solid support as described above are screened for presence or absence of Y chromosomal DNA by in situ hybridization using a nucleic acid probe which is specific for the Y chromosome. Presence of hybridization of the Y chromosome-specific probe is indicative of a male fetus whereas absence of hybridization is indicative of a female fetus.

The following is a description of the present method of enriching for and separating fetal granulocytes present in the blood of a pregnant woman and, subsequently, separating fetal nucleic acid from maternal nucleic acid, and the present method of prenatal detection (presence/absence or quantitation) of selected nucleic acid in fetal cells.

I. Enrichment for Granulocytes Within a Sample of Maternal Blood

One of the first steps in developing the present method of isolating fetal granulocytes from a maternal blood sample was identification of monoclonal antibodies that permit identification and separation of fetal granulocytes from maternal cells present in blood obtained from a pregnant woman. This has been done, as described in detail in Example 1. As a result, it has been determined that monoclonal antibodies which recognize fetal cell surface antigens are useful in separating fetal granulocytes and maternal cells. The following is a brief description of monoclonal antibodies which have been shown to be useful in separating fetal granulocytes from maternal cells present in a maternal blood sample. However, other monoclonal antibodies which distinguish between fetal granulocytes and maternal cells on the basis of surface antigenic differences, can also be used in the present method.

A. Antibodies and Antibody Treatment

The present method utilizes at least one type of antibody which recognizes and binds to a surface antigen present on fetal granulocytes, and/or at least one type of antibody which recognizes and binds to a surface antigen present on maternal cells, but neither antibody may be specific for both fetal and maternal cells. That is, the present method can be carried out using one or more antibodies which distinguish fetal granulocytes from maternal cells. The present method can be carried out using whole blood or blood treated or processed to enrich for (increase the concentration of) nucleated cells including fetal granulocytes.

Described below is the selection and successful use of monoclonal antibodies which distinguish fetal granulocytes from maternal cells. As described in detail in Example 1, a combination of two monoclonal antibodies were used to distinguish fetal granulocytes from maternal cells. One antibody which can be used, an anti-CD71, recognizes CD71 which is the transferrin receptor (TfR). Erythroblasts have been shown to express the transferrin receptor (Loken, M. R., et al., *Blood*, 69, 255–263 (1987)) on their cell surfaces from the BFU-E stage until nuclear extrusion (Loken, M. R. et al., *Blood*, 69, 255–263 (1987)). The transferrin receptor has also been shown to be present on activated lymphocytes (Trowbridge, I. S. and M. B. Omary, *Proc. Natl. Acad Sci. USA*, 78, 3039–3043 (1981)), certain tumor cells (Greaves, M. et al., *Int. J. Immunopharmac.*, 3,283–300 (1981)), and trophoblast cells (Galbraith, G. M. P. et al, *Blood*, 55, 240–242 (1980)). Thus, such an antibody recognizes and binds to fetal nucleated cells but not maternal leukocytes. Although the antibody is not specific for fetal granulocytes, it can be used together with a second antibody to facilitate separation of and enrichment for fetal granulocytes. As described in Example 1, a commercially available fluorescein-conjugated monoclonal antibody against the transferrin receptor was used to separate fetal nucleated cells including fetal granulocytes from maternal cells.

In addition to an anti-CD71 antibody, a second monoclonal antibody, which recognizes and binds to glycophorin A, was used to facilitate separation of and enrichment for fetal granulocytes. Glycophorin A is a sialoglycoprotein known to be present on the surface of all committed erythrocytes. The combination of the anti-CD71 antibody and the anti-glycophorin A antibody allowed for labelling of and subsequent separation of a subpopulation of cells derived from a maternal peripheral blood sample which included fetal granulocytes and fetal granulocyte precursors. Isolation of granulocytes can be confirmed by staining cells with a DNA dye, such as 4,6-diamidino-2-phenyl-indole (DAPI), and analyzing their morphology microscopically. Granulocytes have a unique tri-lobed nucleus that allows for definitive identification of this cell type.

Other monoclonal antibodies, or combinations of monoclonal antibodies, which are able to distinguish between fetal granulocytes and maternal cells present in a maternal blood sample can also be used. For example, a combination of an anti-CD36 monoclonal antibody, which recognizes the thrombospondin receptor, and an anti-glycophorin A monoclonal antibody can be used to facilitate separation of and enrichment for fetal granulocytes and granulocyte precursors. The thrombospondin receptor is known to be present on lymphocytes, platelets and nucleated erythrocytes and therefore is not specific for fetal granulocytes. However, when used together with an anti-glycophorin A antibody, an anti-CD36 monoclonal antibody is effective for separation of and enrichment for fetal granulocytes and granulocyte precursors from a maternal blood sample.

Antibodies which can be used include commercially available monoclonal antibodies and those which can be produced using known techniques. For example, a monoclonal antibody which recognizes a granulocyte-specific cell surface antigen may be used alone or in combination with other antibodies to facilitate separation of and enrichment for fetal granulocytes. Monoclonal antibodies which recognize and bind to cell surface molecules known to be present on granulocytes can be used, including antibodies against CD11c, CD13, CD15, CD33, CD34 and CD67. Additionally, a monoclonal antibody specific for a granulocyte surface antigen can be produced by using a granulocyte, preferably a fetal granulocyte, as an immunogen followed by known hybridoma techniques in order to produce and identify a monoclonal antibody specific for granulocytes.

Alternatively, one or more monoclonal antibodies which are specific for maternal cells (that is, which recognize and bind to a cell surface marker present on maternal cells, e.g. maternal leukocytes, but not present on fetal granulocytes) can be used to facilitate removal of maternal cells from the sample of maternal blood, thereby separating fetal granulocytes from maternal cells and resulting in an enrichment of fetal granulocytes in the cell population from which the maternal cells were removed. For example, a monoclonal antibody HLe-1 (Becton-Dickinson Monoclonal Center, Mountain View, Calif., catalog #7463) recognizes and binds to an antigen present on mature human leukocytes and can be used to remove maternal cells from a maternal blood sample. See PCT Publication WO 91/07660. A monoclonal antibody which recognizes and binds to maternal cells but not fetal granulocytes can be combined with a monoclonal antibody which recognizes and binds fetal granulocytes but not maternal cells in order to both remove maternal cells and to facilitate enrichment for fetal granulocytes.

Monoclonal antibodies are contacted with cells in the maternal blood sample using standard techniques for immunofluorescent staining of cells. One or more antibodies at an appropriate concentration is incubated with the cells on ice for a period of time, usually in the range of 30 minutes, and the cells are then washed with an isotonic buffer such as phosphate buffered saline (PBS) in order to remove any antibodies which have not specifically bound to cells.

Reagents other than monoclonal antibodies can be used to label fetal granulocytes in order to enrich for and separate them from maternal blood. The requirement is that the reagent can bind to fetal granulocytes and can be detected in a way that allows for fetal granulocyte enrichment and/or separation. For example, a soluble ligand for a receptor on fetal granulocytes can be fluorescently labelled and used to label fetal granulocytes such that they can be separated from maternal cells by flow cytometry. Alternatively, a soluble immunoglobulin fusion protein of a ligand for a receptor on fetal granulocytes (that is, a ligand to which a constant region of an immunoglobulin has been fused) could be used to bind to fetal granulocytes and the bound ligand could then be detected with an fluorescently-labelled anti-immunoglobulin antibody in order to facilitate enrichment and separation of the fetal granulocytes by flow cytometry.

B. Pretreatment of Maternal Blood Before Antibody Treatment

Separation of fetal granulocytes from a maternal blood sample using antibodies as described above can be carried out with samples of whole blood or a fraction of whole blood (i.e., one resulting from treatment or processing of whole blood to increase the proportion of fetal nucleated cells present), referred to as a nucleated cell enriched sample. A nucleated cell enriched sample can be produced, for example, by separating non-nucleated cells from nucleated cells within the maternal blood sample, resulting in a nucleated cell enriched sample. One method for separating non-nucleated cells from nucleated cells is by density gradient centrifugation, which separates cells on the basis of cell size and density. The maternal blood sample is subjected to density gradient centrifugation using a density gradient material. Appropriate commercially available density gradient materials include Ficoll, Ficoll-Hypaque, Histopaque, Nycodenz and Polymorphprep. After centrifugation, the maternal blood sample is separated into a supernatant layer, which contains platelets; a mononuclear cell layer; and an agglutinated pellet which contains non-nucleated erythrocytes. The mononuclear layer is separated from the other layers, to produce a nucleated cell enriched sample from which non-nucleated cells have been removed and which is enriched in nucleated cells. The density gradient solution Polymorphoprep separates whole blood into an additional layer which is specifically enriched in granulocytes. Thus, this particular gradient can be used to enrich for fetal granulocytes, either before an additional antibody-mediated enrichment step or, if sufficient enrichment is achieved to detect fetal granulocytes in the granulocyte layer, instead of an antibody-mediated enrichment step.

Another alternative to mononuclear cell isolation for production of a nucleated cell enriched sample is to selectively lyse maternal non-nucleated erythrocytes. Cells in the maternal blood sample can be incubated in one of a number of hypotonic buffers known to be effective, and conventionally used, for lysing nonnucleated erythrocytes, such as 0.17M NH$_4$Cl, 0.01M Tris, pH 7.3. Buffers suitable for this purpose are also available commercially (e.g. "Lyse and Fix", GenTrak).

II. Separation of Fetal Granulocytes from Maternal Cells in Maternal Blood

The maternal blood sample, whether maternal whole blood or a nucleated cell enriched sample, is subjected to separation, based on surface antigenic differences between fetal granulocytes and maternal cells using antibodies described above. The maternal sample is contacted with at least one monoclonal antibody which is specific for either fetal granulocytes or maternal cells, but not for both, thus making it possible to separate the two types of cells. The maternal blood sample can be combined with a single monoclonal antibody or multiple monoclonal antibodies having differing specificities. A combination of monoclonal antibodies can be designed to enhance separation of cell types beyond that possible with a single monoclonal antibody. For example, as described above, a combination of two antibodies, neither of which is granulocyte specific, can be used to separate and enrich for fetal granulocytes based upon their reactivity with both antibodies. Alternatively, one antibody which is specific for fetal cells can be used together with another antibody which is specific for maternal cells. The fetal cell-specific antibody is used for "positive selection", that is, to select for and therefore enrich for fetal cells while the maternal-specific antibody is used for "negative selection", that is, to remove maternal cells from the sample, thereby further enriching for fetal cells in the remaining sample.

Following contacting the maternal blood sample, or fractionated sample thereof, with one or more monoclonal antibodies, separation of the fetal cells is carried out using known techniques, such as flow cytometry, binding of cells to immunomagnetic beads or cell panning. In general, the monoclonal antibodies are associated with a detectable label (e.g., radioactive material, fluorophore). This label may be conjugated directly to the monoclonal antibody with which the cells are contacted (the primary antibody) or it can be attached to a second antibody (a secondary antibody) which is specific for and recognizes the primary antibody, for example an anti-immunoglobulin constant region antibody. When cells are contacted with a combination of two or more primary antibodies, these antibodies can be labelled such that they can be distinguished from each other, e.g. each antibody can be labelled with a different fluorophore. A cell which is bound by multiple antibodies can then be identified by the presence of fluorescence from each of the different fluorophores associated with the cell.

Flow cytometry can be performed on fluorescently labelled cells using a fluorescent activated cell sorter (also called a flow cytometer). Cells treated with one or more fluorescently labelled antibodies are passed through a laser beam and fluorescent cells can be physically deflected into a test tube or onto a slide for collection. When a single fluorescently labelled antibody is used, labelled cells can be separated from unlabelled cells by sorting for each population. When two antibodies are used, each labelled with a different fluorophore, cells positive for one or the other fluorophore or positive for both fluorophores can be separated from unlabelled cells by sorting for each population. In addition to sorting cells based upon fluorescence, flow cytometry can further be used to characterize cells to permit identification of different cell types within a mixed cell population. When cells pass through the laser beam of a flow cytometer, laser light is scattered. This scattering can be converted to an electronic signal to produce a scatter profile. The scatter profile is a composite of two parameters: forward angle light scatter and side scatter. Forward angle light scatter is influenced by cell size whereas side scatter is influenced by cell granularity. Different cell types generate different, characteristic scatter profiles. Granulocytes generate a characteristic scatter profile which can be detected and used to demonstrate the presence of granulocytes in a sorted cell population.

In addition to analyzing cells types based upon their scatter profile, it is possible to sort for particular cells types in a mixed cell population based upon their differing scatter profiles. Thus, fetal granulocytes in a cell population containing other cell types (e.g. fetal nucleated erythrocytes) can be separated from other cell types based upon the characteristic scatter profile of granulocytes and therefore can be further enriched by sorting on this basis.

It is also possible to separate fetal granulocytes from maternal cells by means other than flow cytometry and to subsequently analyze fetal granulocyte nucleic acid obtained in this way. Such separation procedures may be used in conjunction with or independent of flow cytometry. This is advantageous because lack of access to a flow cytometer, as well as expense, could limit potential applications of this technique. Thus, other methods of fetal cell separation can be used. The separation method used can result in elimination of unwanted cells ("negative selection") or isolation of rare but desirable cells ("positive selection").

In one embodiment, maternal cells are depleted prior to fetal cell isolation. The mononuclear cell layer is initially isolated from a maternal blood sample, for example following Ficoll-Hypaque density gradient centrifugation. The resulting cell suspension consists predominantly of maternal cells. In order to increase the eventual proportion of fetal cells present thereby enriching for fetal cells, maternal cells are selectively removed by incubating the cells with antibodies which recognize and bind maternal cells and which are attached to a solid support. Such supports include magnetic beads, plastic flasks, plastic dishes and columns. The antibodies recognize and bind antigens present on the cell surface of maternal cells, e.g. an antibody specific for an antigen present on human mature leukocytes can be used. Thus, a majority of maternal cells are eliminated by virtue of being bound to the solid support. The total number of cells remaining in the cell suspension is smaller, but the proportion of fetal cells present is larger than was present in the starting sample.

Separation of fetal granulocytes can be achieved by use of immunomagnetic beads or by cell panning can also be used. In this embodiment, the mononuclear cell layer is isolated, as described previously. This layer is then mixed with antibody-coated polymer particles containing magnetic cores (e.g., "Dynabeads"). These immunomagnetic beads are commercially available (Dynal AS, Oslo, Norway) coated with a variety of antibodies which can be used as a "primary antibody" for direct contact with cells of a maternal blood sample. For example, immunomagnetic beads coated with an antibody to a human mature leukocyte antigen can be used for negative selection of maternal cells. Alternatively, immunomagnetic beads coated with a variety of antibodies which can be used as a "secondary antibody", based upon their ability to recognize and bind to a primary antibody, are also commercially available (Dynal AS, Oslo, Norway). For example, immunomagnetic beads coated with an antibody specific for mouse immunoglobulins can be used when the primary antibody is a mouse immunoglobulin. Immunomagnetic beads coated with a secondary antibody can either be preincubated with the primary antibody in the absence of cells to form a primary-secondary antibody complex which is capable of binding cells for which the primary antibody is specific or the primary antibody can be contacted with cells in solution and then the primary antibody-cell mixture can be contacted with the secondary antibody-coated immunomagnetic beads.

After contacting cells with an antibody-coated immunomagnetic bead, antibody-bound cells are isolated with a magnetic particle concentrator (e.g. a magnet). In one embodiment, two sets of antibody-coated immunomagnetic beads are used in succession for "negative selection" of cells followed by "positive selection" of cells. First, cells from a maternal blood sample are contacted with immunomagnetic beads specific for maternal cells, e.g. maternal leukocytes, and maternal cells are depleted from the sample by removing cells which bind to these immunomagnetic beads (negative selection). Next, the remaining cells are contacted with immunomagnetic beads which allow for binding of fetal granulocytes and the fetal granulocytes are isolated by collecting cells which bind to these immunomagnetic beads (positive selection). For example, two mouse monoclonal antibodies, one against CD71 and one against glycophorin A, can be preincubated with immunomagnetic beads coated with a monoclonal antibody specific for mouse immunoglobulins (e.g. an antibody which recognizes an appropriate mouse immunoglobulin constant region such as an IgG constant region) and these immunomagnetic beads are then contacted with the remaining cells (from which maternal cells have been removed).

Mueller et al. (*Lancet*, 336, 197–200 (1990)) have described a method of isolating placenta-derived trophoblast cells in the blood of pregnant women using magnetic beads. This method included mixing 1 ml of monoclonal antibody hybridoma culture supernatant with 2×10⁷ magnetic beads precoated with sheep antibody to mouse IgG (Fc fragment) (Dynabeads M-450, Dynal AS, Oslo, Norway), and incubating overnight at room temperature. The coated beads were stored at 4° C. and washed three times in ice-cold RPMI 1640 medium containing lithium heparin (10 IU/ml). The blood from the pregnant women was collected into tubes containing 10 IU of lithium per ml of whole blood, diluted 1:10 with RPMI containing lithium, and incubated with the antibody coated beads at 4° C. overnight. The desired cells were bound to the antibody on the beads; the bead-bound cells were then collected by means of a cobalt-samarium magnet. Although in this case the antibody was directed against trophoblast antigens a similar technique can be utilized with, for example, an antibody specific for a cell surface antigens present on fetal granulocytes and not present on maternal cells. An advantage to this particular technique is that an initial step which results in mononuclear cell isolation is not added. Additionally, the magnetic beads can be used for both positive (fetal cells) and negative (maternal cells) selection.

An alternative method of isolation can be a modification of the method described by R. J. Berenson et al. (*J. of Immunol. Methods*, 91(1986)) in which the high affinity between the protein avidin and the vitamin biotin was exploited to create an indirect immuno-adsorptive procedure. In this technique, avidin was linked to cyanogen bromide activated sepharose 6 MB beads and washed in an alternating fashion with coupling buffer (0.1M NaHCO₃ in 0.5M NaCl at pH 8.3), and washing buffer (0.1M sodium acetate in 0.5M NaCl at pH 4.5) and stored at 4° C. Blood cells were incubated with 1 ) murine monoclonal antibody, and 2) biotinylated goat anti-mouse immunoglobulin. A 3 ml column of avidin-linked gel was packed in a Pharmacia K 19/15 column. The treated cells were passed through the column in phosphate buffered saline containing 2% bovine serum albumin. Cells which bound the murine monoclonal antibody adhered to the column based upon the interaction of biotin with avidin, wherein the biotinylated goat anti-mouse immunoglobulin acted as a "bridge" between the cells and the column. Adherent cells were subsequently dislodged from the column by mechanical agitation and recovered. This technique can be applied to fetal granulocyte separation if the antibodies used recognize fetal granulocyte surface antigens or maternal cell surface antigens, but not both. Variation in methods for conjugating antibodies to beads exist; examples include those described by Thomas and co-workers (Thomas, T. E., et al. (*J. of Immuno. Methods*, 120, 221-131 (1989)) and by deKretser and co-workers (deKretser, T. A., et al. (*Tissue Antigens*, 16, 317-325 (1980)). The use of an antibody-bound column does not require the preliminary isolation of the mononuclear cell fraction from whole blood.

Other methods of separating fetal granulocytes from maternal cells can also be used, provided that they make it possible to differentiate between fetal cells and maternal cells, and to isolate one from the other.

III. Detection of Fetal Nucleic Acid in Maternal Blood

Following enrichment for and separation of fetal granulocytes from a maternal blood sample, the fetal granulocytes can be used as a source of fetal nucleic acid for analyses such as determination of fetal gender, detection of a genetic disease in the fetus or detection of a chromosomal abnormality in the fetus. Fetal nucleic acid in fetal granulocytes, isolated as described herein or by other means by which fetal granulocytes can be separated from a maternal blood sample, can be analyzed or assessed for the occurrence of a nucleic acid of interest for diagnostic or other purposes. The nucleic acid which is to be detected in fetal cells is referred to herein as a nucleic acid of interest. For example, the nucleic acid of interest whose presence or absence is to be determined and whose quantity can also be determined may be a gene for a disease, such as cystic fibrosis, where the causative gene or gene portion has been cloned and sequenced; alternatively, the nucleic acid of interest may be X- or Y-chromosome-specific DNA. The same procedure can also be used, with appropriate modifications (e.g., an appropriate nucleic acid probe, time, temperature), to detect other genes or gene portions. The nucleic acid detected in fetal granulocytes, that is, the nucleic acid of interest, can be DNA, e.g. chromosomal DNA or a particular gene fragment within chromosomal DNA or amplified from chromosomal DNA, or can be RNA, e.g. mRNA. The labelled probe used to detect the nucleic acid of interest can be, for example, a labelled DNA probe, a labelled RNA probe or labelled oligonucleotides.

Fetal granulocytes are treated such that fetal nucleic acid is made available for detection. Appropriate treatments that can be used, depending on the method used for detection of fetal nucleic acid. For example, fetal DNA can be made available by boiling the fetal granulocytes to lyse them, thereby releasing fetal DNA, for instance prior to amplification of fetal DNA. Fetal granulocytes can be attached to a solid support, e.g. a microscope slide, in such a way that fetal nucleic acid is made available, for example by fixing fetal granulocytes or granulocyte nuclei to a microscope slide prior to in situ hybridization. The fetal granulocytes or portions thereof (e.g. nuclei) which are attached to a solid support such that fetal nucleic acid is made available is referred to as fetal granulocyte material. Fetal nucleic acid in fetal granulocytes (or fetal granulocyte material) can be detected directly, for example by in situ hybridization of a labelled nucleic acid probe complementary to a nucleic acid of interest or the fetal nucleic acid can be amplified prior to detection using a known amplification technique such as the polymerase chain reaction (PCR). Primers for PCR amplification are chosen which specifically amplify a DNA of interest in the fetal DNA If in situ hybridization is to be carried out, fetal granulocytes are separated onto a solid support, such as a microscope slide, such that fetal nucleic acid is available for detection. In situ hybridization can be used, for example, to detect Y chromosome-specific sequences in fetal DNA in order to determine the gender of a fetus as described in greater detail in Example 2. In situ hybridization can also be used to assess chromosomal abnormalities in a fetus, including chromosomal aneuploidies, such as a trisomy, or chromosomal rearrangements or deletions, as described in greater detail in Example 4.

Fetal DNA can be amplified by PCR as described in detail in Example 3. If amplification is to be carried out, fetal granulocytes can be lysed by boiling and fetal DNA can then be amplified for an appropriate number of cycles of denaturation and annealing (e.g., approximately 24–60). Control samples include a tube without added DNA to monitor for false positive amplification. With proper modification of PCR conditions, more than one separate fetal gene can be amplified simultaneously. This technique, known as "multiplex" amplification, has been used with six sets of primers in the diagnosis of DMD (Chamberlain, J. S., et al., *Prenat. Diagnosis*, 9, 349–355 (1989)). When amplification is carried out, the resulting amplification product is a mixture which contains amplified fetal DNA of interest (i.e., the DNA whose presence is to be detected and/or quantitated) and other DNA sequences. The amplified fetal DNA of interest and other DNA sequences are separated, using known techniques, for example by gel electorphoresis. Subsequent analysis of amplified DNA can be carried out using known techniques, such as: digestion with a restriction endonuclease, ultraviolet light visualization of ethidium bromide stained agarose gels, DNA sequencing, or hybridization with a labelled DNA probe, for example, allele specific oligonucleotide probes (Saiki, R. K., et al, *Am. J. Hum. Genet.*, 43 (Suppl):A35(1988)). Amplification of and hybridization to allele-specific sequences can determine whether polymorphic differences exist between the amplified "maternal" and "fetal" samples and can be used to identify a female fetus based upon detection of paternal polymorphisms in the fetal DNA. DNA sequences from the father can be identified in the autosomal chromosomes of the fetus. Consequently, the method of the present invention can be used to separate and identify female fetal granulocytes, as well as male fetal granulocytes, from maternal blood. Thus, the method can be used for all nucleic acid-based diagnostic procedures currently being achieved with other methods, such as amniocentesis.

In one embodiment, the amplification mixture is separated on the basis of the size of the nucleic acid fragments and the resulting size-separated fetal nucleic acid is contacted with an appropriate selected nucleic acid probe or probes (nucleic acid sufficiently complementary to the nucleic acid of interest that it hybridizes to the nucleic acid of interest in fetal nucleic acid under the conditions used). Generally, the nucleic acid probes are labelled (e.g., with a radioactive material, a fluorophore or other detectable material). After the size-separated fetal nucleic acid and the selected nucleic acid probes have been maintained for sufficient time under appropriate conditions for hybridization of complementary nucleic acid sequences to occur, resulting in production of fetal nucleic acid/nucleic acid probe complexes, detection of the complexes is carried out using known methods. For example, if the probe is labelled, a fetal nucleic acid/labelled nucleic acid probe complex can be detected and/or quantitated (e.g., by autoradiography, detection of the fluorescent label). The quantity of labelled complex (and, thus, of fetal nucleic acid) can be determined by comparison with a standard curve (i.e., a predetermined relationship between the quantity of label detected and a given amount of nucleic acid present).

As used in a diagnostic context, such as to detect a gene containing a mutation known to cause a genetic disease such as cystic fibrosis, the present method is carried out as follows: Initially, a maternal blood sample (typically 20 ml.) is obtained and separated into component layers based on cell size and density (e.g. by Ficoll-Hypaque density gradient centrifugation) to remove non-nucleated erythrocytes and produce a mononuclear cell layer. This results in production of a nucleated cell enriched sample which includes fetal granulocytes. The nucleated cell enriched sample is stained with at least one appropriate monoclonal antibody (e.g., one which allows for separation of fetal granulocytes from the sample). For example, a granulocyte-specific monoclonal antibody can be used. In general, the monoclonal antibody bears a detectable label. Alternatively, a combination of monoclonal antibodies which recognize fetal granulocytes, such as an anti-CD71 (anti-TfR) antibody and an anti-glycophorin A antibody, as described above, can be used, each labelled with a different fluorescent compound. Additionally, one or more monoclonal antibodies specific for maternal cells can be used to remove essentially all maternal cells. Labelled cells are subsequently separated from unlabelled or differently labelled cells using a known method, such as flow cytometry. Binding of the monoclonal antibodies to cells for which they are specific results in production of labelled monoclonal antibody-cell complexes. For example, in the case in which anti-CD71 (anti-TfR) antibodies and anti-glycophorin A antibodies are used, fetal granulocytes are bound by both antibodies, to produce fetal granulocyte/anti-CD71/anti-glcophorin A antibody complexes. The fetal granulocyte/anti-CD71/anti-glycophorin A complexes are separated from maternal cells by, for example, fluorescent activated cell sorting. After separation, the fetal cells are lysed to produce crudely extracted fetal DNA which is subsequently amplified, using, for example, PCR. This results in production of amplified fetal DNA, which can be subsequently separated on the basis of size. Size-separated fetal DNA is contacted with a labelled DNA probe complementary to a nucleic acid of interest. For example, for prenatal detection of cystic fibrosis, a labelled DNA probe complementary to the gene associated with cystic fibrosis can be used. A suitable probe is described in Newton, C. R., et al. *Lancet* 2, 1481–1483 (1989). If the fetal DNA contains the nucleic acid of interest (e.g. the gene associated with cystic fibrosis), fetal DNA/labelled probe complexes are formed and can be detected.

Fetal DNA/labelled probe complexes are subsequently detected, using a known technique, such as autoradiography. Simple presence or absence of hybridization of the nucleic acid probe complementary to a nucleic acid of interest and the fetal DNA can be determined or the quantity of fetal DNA containing the nucleic acid of interest can be determined. The result is a qualitative or quantitative assessment of fetal DNA obtained from a maternal blood sample. For many genes which may carry a disease-causing mutation, probes are available which detect a restriction-site polymorphism which is indicative of the presence of a disease-causing mutation within the gene. Detection of such a restriction site polymorphism in fetal DNA using a nucleic acid probe specific for a gene associated with a disease of interest is indicative that the fetal DNA carries a mutation in the gene and therefore that the fetus has the disease.

The presence of fetal nucleic acid associated with diseases or conditions other than cystic fibrosis can also be detected and/or quantitated by the present method. In each case, an appropriate probe is used to detect the sequence of interest. For example, sequences from probes St14 (Oberle, I., et al., *New Engl. J. Med.*, 312, 682–686 (1985)), 49a (Guerin, P., et al., *Nucleic Acids Res.*, 16, 7759 (1988)), KM-19 (Gasparini, P., et al., *Prenat. Diagnosis*, 9, 349–355 (1989)), or the deletion-prone exons for the Duchenne muscular dystrophy (DMD) gene (Chamberlain, J. S., et al., *Nucleic Acids Res.*, 16, 11141–11156 (1988)) are used as probes. St14 is a highly polymorphic sequence isolated from the long arm of the X chromosome that has potential usefulness in distinguishing female DNA from maternal DNA. It maps near the gene for Factor VIII:C and, thus can also be utilized for prenatal diagnosis of Hemophilia A. Primers corresponding to sequences flanking the six most commonly deleted exons in the DMD gene, which have been successfully used to diagnose DMD by PCR, can also be used (Chamberlain, J. S. et al., *Nucleic Acids Res.*, 16, 11141–11156(1988)). Other conditions which can be diagnosed by the present method include β-thalassemia (Cai, S.-P., et. al., *Blood*, 73:372–374 (1989); Cai, S.-P., et al., *Am. J. Hum. Genet.*, 45:112–114 (1989); Saiki, R. K., et al., *New Engl. J. Med.*, 319, 537–541 (1988)), sickle cell anemia (Saiki, R. K., et al.,

*New Engl. J. Med.*, 319, 537–541 (1988)), phenylketonuria (DiLella, A. G., et al., *Lancet*, 1,497–499 (1988)) and Gaucher disease (Theophilus, B., et al., *Am. J. Hum. Genet.*, 45, 212–215 (1989)). An appropriate probe (or probes) is available for use in the present method for assessing each condition.

A kit for use in carrying out the present method of isolating and detecting fetal nucleic acid of interest, such as a chromosomal abnormality associated with a disease or other condition, in a maternal blood sample can be produced. It includes, for example, a container for holding the reagents needed; the reagents and, optionally, a solid support for use in separating fetal granulocyte/specific antibody complexes from other sample components or for removing maternal cells complexed with a specific antibody. For example, reagents in a kit to be used in detecting nucleic acid of interest after amplification of fetal DNA by PCR can include: 1) at least one antibody specific for a surface antigen characteristic of fetal granulocytes but not specific for a surface antigen characteristic of maternal leukocytes; selected DNA primers for use in amplifying fetal DNA by PCR; and at least one nucleic acid probe complementary to the nucleic acid to be detected (the nucleic acid of interest). The kit, as indicated, can also include a solid support to be used in separating complexes formed from other samples components. Such solid support can be, for example, a glass slide such as a microscope slide, nitrocellulose filter, or immunomagnetic beads and can have affixed thereto an antibody selective for the antibody present in the fetal granulocyte/specific antibody complexes.

The present invention will now be illustrated by the following examples, which are not intended to be limiting in any way. The contents of all references and published patents or patent applications cited throughout the application are hereby incorporated by reference.

EXAMPLE 1

Enrichment for and Separation of Fetal Granulocytes from Maternal Blood

A 20 ml sample of peripheral blood from a pregnant woman (a maternal blood sample) was obtained and was collected in ethylenediamine tetraacetic acid (EDTA), diluted 1:3 with Hanks' balanced salt solution, layered over a Ficoll/Hypaque solution (Pharmacia) and spun at 2000 rpm for twenty minutes at room temperature. The mononuclear cell layer was isolated, washed with phosphate buffered saline (PBS) and centrifuged at 1400 rpm for ten minutes at 4° C. The cell pellet, which is enriched for nucleated cells, was recovered and the cells were used for immunofluorescent staining in order to enrich for and separate fetal granulocytes within this cell population.

Isolation of Fetal Granulocytes from Maternal Blood Using Two Monoclonal Antibodies for Immunofluorescent Staining After enriching for nucleated cells in the maternal blood sample, the remaining cells were contacted with two monoclonal antibodies which allowed for further enrichment for fetal cells and separation of fetal cells, in particular fetal granulocytes, by fluorescent activated cell sorting. One of the two monoclonal antibodies used is specific for the transferrin receptor (Newman, R., et al., *Trends Biochem. Sci.* 1,397–399 (1982)). The transferrin receptor (TfR), also called CD71, is a surface glycoprotein important in cellular iron transport. The TfR is present on activated lymphocytes (Trowbridge, I. S., et al., *Proc. Natl. Acad. Sci. USA*, 78, 3039–3043 (1981)), certain tumor cells (Greaves, M. et al., *Int. J. Immunopharmac.*, 3,283–300 (1981)), and trophoblast cells (Galbraith, G. M. P., et al., *Blood*, 55:240–242 (1980)). Erythroblasts express the CD71 on their cell surfaces from the BFU-E stage until nuclear extrusion (Loken, M. R., et al., *Blood*, 69, 255–263 (1987)). Thus, CD71 is an effective target antigen for enrichment of fetal nucleated erythrocytes found in maternal blood. In addition, it has now been discovered that CD71 is also an effective target antigen for enrichment of fetal granulocytes found in maternal blood. A monoclonal antibody against CD71 is available as both a fluorescein isothiocyanate (FITC) conjugate (Becton-Dickinson catalog #7513) and a phycoerythrin (PE) conjugate (gift of Dr. Michael Loken, Becton-Dickinson).

A second monoclonal antibody was used together with the anti-CD71 antibody to contact the nucleated cell enriched sample derived from the maternal blood sample. The second monoclonal antibody was specific for glycophorin A (GPA). Glycophorin A is a sialoglycoprotein present on the surface of all committed erythrocytes and thus is an effective target antigen for enrichment of fetal nucleated erythrocytes found in maternal blood. In addition, it has now been discovered that glycophorin A is also an effective target antigen for enrichment of fetal granulocytes found in maternal blood. A monoclonal antibody against glycophorin A is commercially available as a phycoerythrin conjugate (Coulter Immunology).

Following density gradient centrifugation and isolation of the mononuclear cell layer to form a nucleated cell enriched sample, the nucleated cell enriched sample was contacted with a FITC-labelled anti-CD71 monoclonal antibody and a PE-labelled anti-glycophorin A monoclonal antibody. The cells can be incubated with both antibodies simultaneously or the cells can be contacted with the two antibodies sequentially. Cells were incubated with a 1:10 dilution of commercially supplied antibody in PBS on ice for thirty minutes. The cells were washed once in PBS prior to flow cytometry.

Figure 2:
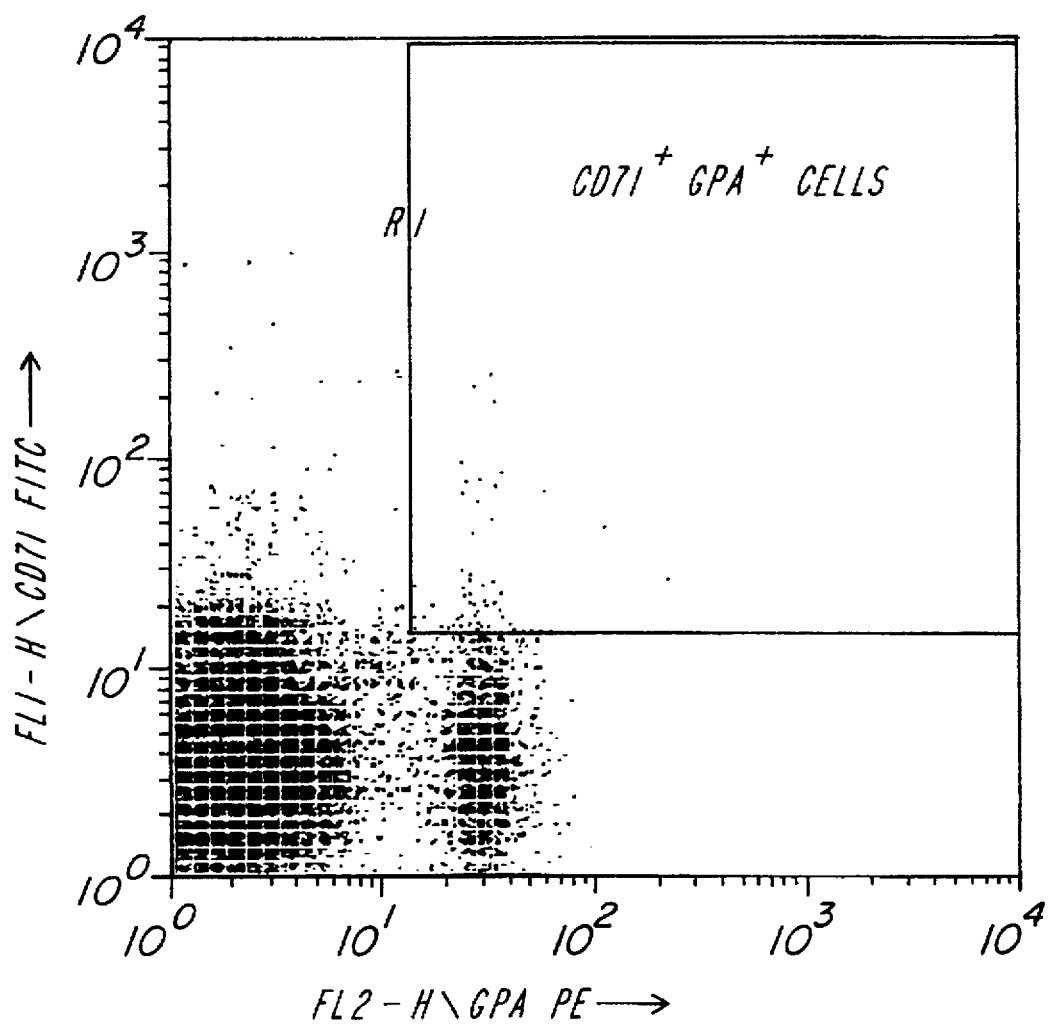
FIG. 2 is a flow cytometric graph depicting the fluorescence of cells present in a nucleated cell enriched sample derived from a maternal blood sample which have been treated with a FITC-labelled anti-CD71 monoclonal antibody and a PE-labelled anti-glycophorin A (GPA) monoclonal antibody. Fluorescence due to binding of anti-GPA is on the X axis and fluorescence due to binding of anti-CD71 is on the Y axis.

Analysis and sorting were performed on a Becton-Dickinson FACS IV with a Consort 40 program as described (Bianchi et al., *Cytometry* 8, 197–202 (1987)). The gain was standardized manually using fluorescent beads and a fluorescein isothiocyanate (FITC) conjugated antibody control, reactive against keyhole limpet hemocyanin, an antigen not expressed on human cells (Becton-Dickinson Catalog No. 9041). A small aliquot of the woman's mononuclear cells were incubated with the antibody control to determine background fluorescence. CD71–/glycophorin A–, CD71+/glycophorin A–, CD71–/glycophorin A+, and CD71+/glycophorin A+cells were determined by physical separation on a logarithmic scale (based upon fluorescence of none, one or both of the two different fluorescent labels on the cells). A flowcytometric graph depicting the different cell populations is shown in FIG. 2. Cells which express both CD71 and glycophorin A on their cell surface bind both antibodies and therefore become labelled with the two distinct fluorescent labels, allowing for their identification and isolation. These cells are the CD71+/glycophorin A+population and will be referred to as "double positive" cells. The double positive cell population, indicated by the boxed region in FIG. 2, was sorted into a 1.5 ml centrifuge tube and used for further analysis.

Since the two antibodies contacted with the nucleated cell enriched sample were known to recognize antigens present on fetal nucleated erythrocytes, it was expected that this cell type would be present in the double positive cell population and therefore would be selected and sorted based upon dual fluorescence. To confirm that this cell type was present in the double positive cell population and to determine whether any other cell types were also present in the double positive cell population, this population was subjected to further flow cytometric analysis. The forward angle light scatter profile, which denotes cell size, and the side scatter profile, which denotes cell granularity, were analyzed. These two criteria allow for different cell types, such as granulocytes, nucleated erthrocytes, monocytes and lymphocytes, to be differentiated from one another based upon differences in cell size and granularity that exist between the different cell types. The scatter profile of cells present in a nucleated cell enriched sample derived from a maternal blood sample is shown in FIG. 1 and the different cell types present in the mixed cell population are indicated.

Figure 3:
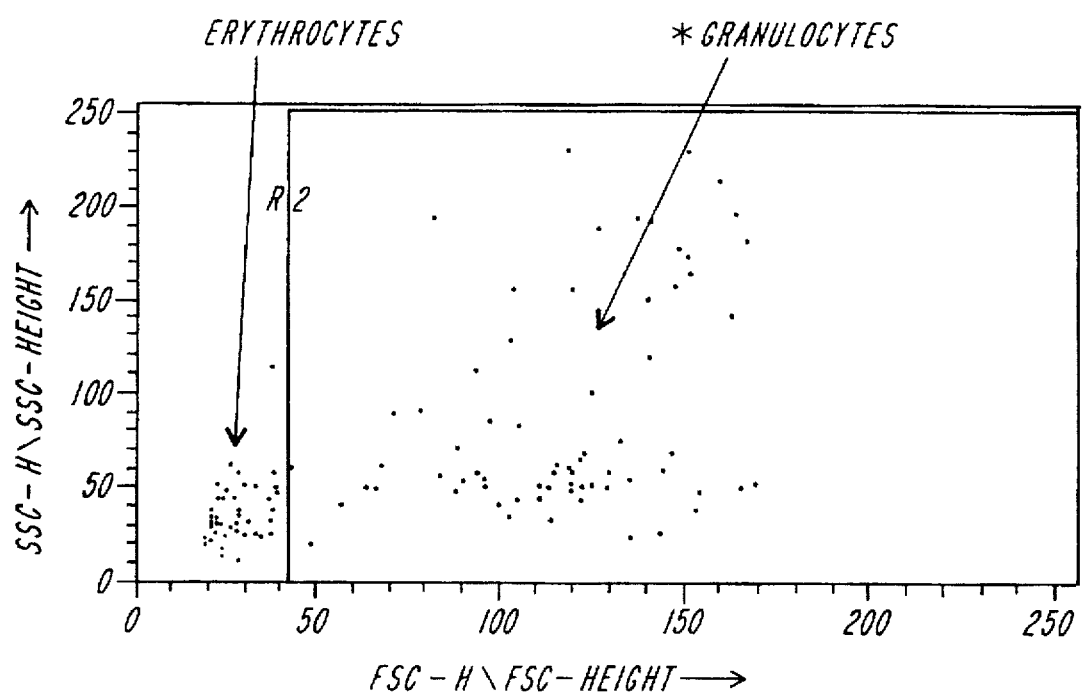
FIG. 3 is a flow cytometric graph depicting the scatter profile of CD71+/GPA+cells isolated from a nucleated cell enriched sample derived from a maternal blood sample by sorting. Forward angle light scatter is on the X axis and side scatter is on the Y axis.

The scatter profile analysis of CD71+/GPA+double positive cells revealed that, in addition to fetal nucleated erythrocytes, the CD71+/GPA+double positive cell population contained fetal granulocytes. The scatter profile of the CD71+/GPA+sorted cell population is shown in FIG. 3, and the erythrocyte and granulocyte populations are indicated. The presence of granulocytes was confirmed by staining the double positive cells with 4,6-diamidino-2-phenyl-indole (DAPI), a DNA dye, and analyzing their morphology under a fluorescent microscope. Granulocytes have a unique trilobed nucleus that allows for definitive identification of this cell type. The sorted, double positive cells derived from maternal blood had a significant number of granulocytes present. The mixed population of sorted double positive (e.g. CD71+/glycophorin A+or CD36+/glycophorin A+) fetal nucleated erthrocytes and granulocytes can be used in subsequent analyses for fetal gender identification and/or diagnosis. Some of the granulocytes were demonstrated to be of fetal origin by detection of Y chromosomal DNA.

Figure 4:
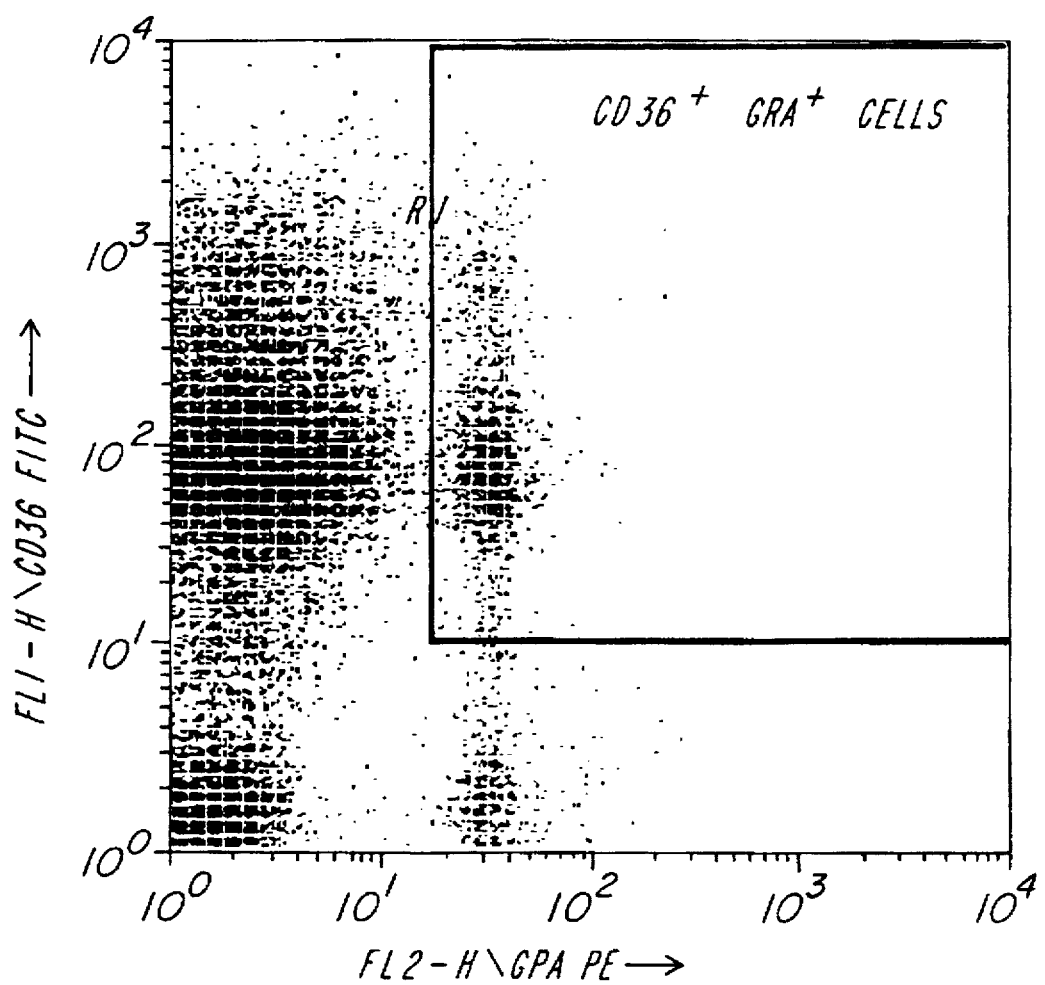
FIG. 4 is a flow cytometric graph depicting the fluorescence of cells present in a nucleated cell enriched sample derived from a maternal blood sample which have been treated with a FITC-labelled anti-CD36 monoclonal antibody and a PE-labelled anti-glycophorin A (GPA) monoclonal antibody. Fluorescence due to binding of anti-GPA is on the X axis and fluorescence due to binding of anti-CD36 is on the Y axis.
Figure 5:
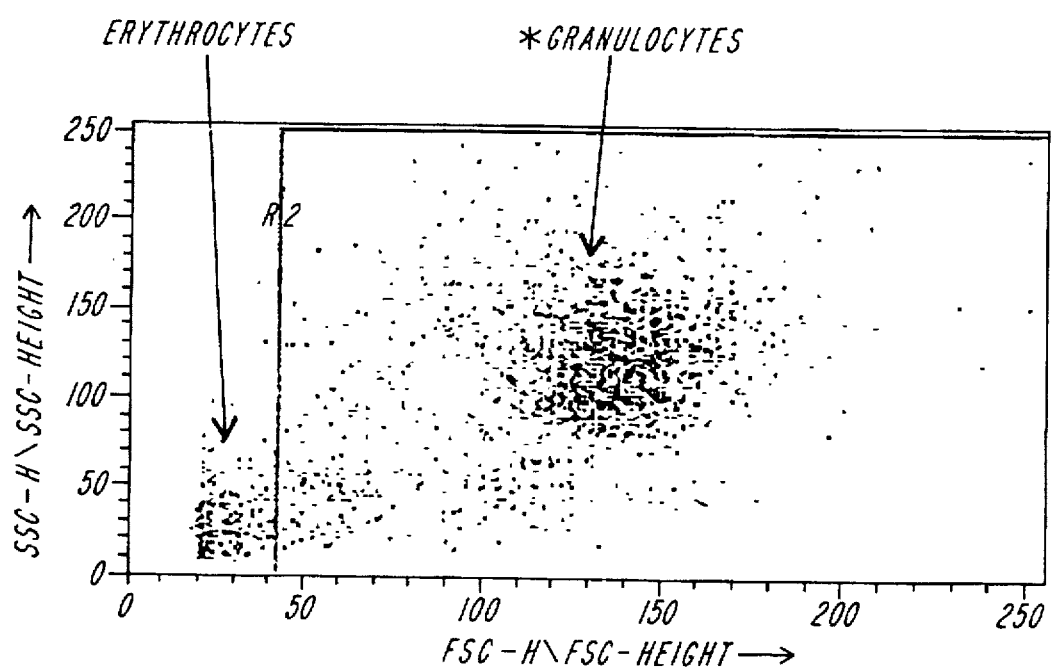
FIG. 5 is a flow cytometric graph depicting the scatter profile of CD36+/GPA+cells isolated from a nucleated cell enriched sample derived from a maternal blood sample by sorting. Forward angle light scatter is on the X axis and side scatter is on the Y axis.

It was further demonstrated that the combined usage of an anti-CD36 monoclonal antibody (reactive with thrombospondin receptor) and an anti-glycophorin A monoclonal antibody to label the nucleated cell enriched sample derived from a maternal blood sample, followed by fluorescent activated cell sorting for the double positive population, also allowed for separation and isolation of fetal granulocytes. A flowcytometric graph depicting the CD36+/GPA+double positive cell population is shown in FIG. 4, with the double positive cell population indicated by a boxed region. Use of these two antibodies also coisolates fetal nucleated erythrocytes. The granulocyte population could be identified based upon its forward angle light scatter and side scatter profile, as depicted in the scatter profile of the CD36+/GPA+ population in FIG. 5, and was subsequently confirmed by morphological identification.

EXAMPLE 2

Detection of Fetal DNA in Granulocytes Isolated from Maternal Blood

To confirm that isolated granulocytes are of fetal origin, fluorescent in situ hybridization can be performed with a DNA probe specific for Y chromosome sequences using granulocytes isolated from a maternal blood sample of a woman known to be pregnant with a male fetus or subsequently independently confirmed to be pregnant with a male fetus. Since Y chromosome sequences in granulocyte DNA must be of fetal origin, hybridization of this probe to the granulocyte DNA is used as an indicator of the fetal origin of the cells and additionally identifies the gender of the fetus as male.

Fluorescence in Situ Hybridization

A granulocyte population is prepared by labelling and sorting cells as described in Example 1. A combination of anti-CD71 and anti-glycophorin A monoclonal antibodies are used to identify and isolate granulocytes, which can then be further isolated from erythrocytes based upon their scatter profile. A solution of methanol and acetic acid (3:1) is used to fix nuclei from sorted cells to glass slides which are then stored at −20° C. (Klinger et al., Am. J. Hum. Genet. 51, 55–65 (1992)). Prior to hybridization, slides are warmed briefly at 60° C. Control hybridizations with male lymphocytes are performed concurrently.

Hybridization to granulocyte DNA can be performed simultaneously with both a Y chromosome-specific probe and an X chromosome-specific probe such that the X chromosome-specific probe functions as an internal control. The two probes are labelled with different fluorescent markers, allowing them to be distinguished. FISH is performed using an X chromosome-specific probe derived from a cosmid containing a pericentromeric repeat sequence of the X chromosome and a Y chromosome-specific probe derived from a cosmid pDP97 containing repetitive sequences. The probes are described in further detail in Klinger et al. Am. J. Hum. Genet. 51, 55–65 (1992). The X chromosome-specific probe is labelled with biotin-dUTP (Sigma) whereas the Y chromosome-specific probe is labelled with digoxigenin-dUTP (Boehringer Mannheim). The probes are hybridized simultaneously as described in Klinger et al. Am. J. Hum. Genet. 51, 55–65 (1992) under suppression conditions (Cremer et al., Hum Genet 80:235–246 (1988); Lichter et al., Hum Genet 80:224–234 (1988)). After overnight hybridization of the probes to the granulocyte DNA on the slides and washing of the slides, the biotin-labelled X-specific probe is detected with avidin conjugated to Texas Red (Vector Laboratories) and the digoxigenin-labelled Y-specific probe is detected with anti-digoxigenin conjugated to fluorescein isothiocyanate (FITC) (Boehringer Mannheim). The slides are mounted in 2.33% DABCO (1,4-diazobicyclo[2.2.2]octane) (Sigma) in 100 mM Tris-HCl, pH 8.0, 90% (v/v) glycerol with 0.5 ug/ml 4,6-diamidino-2-phenyl-indole (DAPI) as a counterstain (Sigma). Slides are analyzed using a Zeiss Axioplan epifluorescence microscope. FITC (producing a green hybridazation signal) and Texas Red (producing a red hybridazation signal) are monitored simultaneously using a dual band pass filter set (Omega Optical, Inc., Brattleboro, Vt.). Images are captured with a cooled confocal digital camera (Photometrics Ltd., Tucson, Ariz.) and image processing is performed with software developed by Recognition Technology, Inc., (Westboro, Mass.).

Detection of both a FITC and a Texas Red signal (i.e. hybridization of both the Y chromosome-specific and the X chromosome-specific probes) to granulocyte DNA is indicative of fetal origin of the granulocyte and, additionally, of a male fetus. Detection of only a Texas Red signal (i.e. hybridization of only the X chromosome-specific probe) is indicative of female fetal origin of the granulocyte, or possibly maternal origin of the granulocyte. A sufficient number of hybridized cells are examined to make a statistically significant determination of the presence of both X and Y chromosome-specific signals or only X chromosome-specific signals in individual granulocytes.

EXAMPLE 3

Use of the Polymerase Chain Reaction to Amplify Gene Sequences in Granulocytes Isolated from Maternal Blood The polymerase chain reaction, or PCR, which has a capacity for making $10^6$ copies of rare target gene sequences, is used to amplify gene sequences in sorted fetal cells. Optimum conditions for PCR, given the minute amounts of DNA expected after a fetal cell sort (approximately 1 pg to 100 ng), were determined. Experimental conditions were modified as new information became available. For example, Taq polymerase was used instead of Klenow fragment of *E. Coli* DNA polymerase (Kogan, S. C. et al., New England J. Med. 317, 990 (1987)) because of its increased specificity in DNA replication.

Initially, studies were performed on repeated sequences from the long arm of the Y chromosome, probe Y431-Hinfa (given by Dr. Kirby Smith, Johns Hopkins University, Baltimore, Md.) and the short arm of the Y chromosome, probe Y411 (Given by Dr. Ulrich Muller, Children's Hospital, Boston, Mass.). Repeated sequences were selected because they would create a stronger amplification signal from a rare male fetal cell. Y411 is identical to Y156 (Muller, U., et al., *Nucleic Acids Res.*, 14, 1325–1329 (1986)), is repeated 10–60 fold, and is absolutely Y specific on Southern blots. Sequence Y43 1 has autosomal homology in females that limited its usefulness in sex determination.

PCR Standardization and Conditions

To define the minimum amount of DNA detectable in maternal blood, a series of standardization experiments were done. DNA from male and female individuals was prepared in tenfold dilutions (1 pg to 1 µg) and amplified using the standard reagents, including reaction buffer, in the Gene-Ampkit (Perkin-Elmer Cetus cat #N801-0055) on a Perkin-Elmer DNA Thermal Cycler. Primers 411-01 and 411-03 were used. These primers are designed to amplify a 222 base pair (bp) sequence detectable with probe Y chromosome-specific probe Y411. The primer sequences are described in detail in Bianchi, D. W., et al. *Proc. Natl. Acad. Sci. USA* 87, 3279–3283 (1990). Other suitable primers are described in Wachtel, S., et al. *Hum. Reprod.* 6, 1466–1469 (1991). The number of amplification cycles varied between 18 and 30. Each amplification cycle consisted of 1 minute at 94° C., 2 minutes at 60° C. and 3 minutes at 72° C., with a 10 minute extension in the last cycle. Amplified DNA samples were electrophoresed on agarose gels, transferred to nylon filters, and hybridized to $^{32}$ P-labelled Y411 probe. While it appeared possible to detect Y specific bands on autoradiographs in lanes containing as little as 10 pg of male DNA, results were often muddled by the presence of amplified DNA in female lanes or control lanes containing no added DNA. The phenomenon of "false positive amplification" has now received universal recognition (Lo, Y-M.D., et al., *Lancet*, 2, 697 (1988); Kwok, S., et al, *Nature*, 339, 237–238 (1989)).

Elimination of "False Positive" Amplification

Due to the limited amount of starting material in a fetal cell sort, every effort was made to eliminate background amplification in order to determine which fetuses truly possess Y chromosomal DNA. Thus, measures were taken to prevent aerosol contamination of male DNA. All PCRs were performed under sterile conditions, wearing gloves, and using positive displacement pipettes. All reagents were prepared in a sterile manner and incubated overnight prior to PCR with a restriction endonuclease having a digestion site within the target sequence. These precautions resulted in a significant decrease and virtual absence of false positive amplification, as monitored by running control reactions with all reagents but no DNA.

Isolation and Amplification of Fetal Gene Sequences from Granulocytes in Maternal Blood After eliminating sources of DNA contamination and determining that as little as 10 pg of male DNA (1 cell 7 pg of DNA) could be detected after PCR amplification, granulocytes from maternal blood are sorted and isolated as described in Example 1. A combination of anti-CD71 and anti-glycophorin A monoclonal antibodies are used to identify and isolate granulocytes, which can then be further isolated, if necessary, from fetal nucleated erythrocytes based upon their scatter profile. Prior to amplification, the cells are lysed by boiling which makes the granulocyte DNA available for amplification. The granulocyte DNA is amplified for the 222 bp sequence in probe Y411 as proof that the cells are derived from the fetus in male pregnancies. The conditions used, as described above, make it possible to detect a minimum of 100 pg of fetal DNA, or the equivalent of 15 fetal cells. The limit of sensitivity can be improved by extending the number of cycles used in PCR.

To further decrease false positive amplification and permit detection of fetal DNA at the single cell level on agarose gels, PCR is carried out using primers derived from a single copy of sequence specific for the long arm of the Y chromosome, PY49a (Guerin, P., et al., *Nucleic Acids Res.*, 16, 7759 (1988)). In preliminary experiments using 60 cycles of PCR, Y chromosomal DNA is visible on ethidium-bromide stained agarose gels. This extraordinary degree of sensitivity can now be applied to DNA from sorted fetal granulocytes.

EXAMPLE 4

Detection of Chromosomal Abnormalities in Granulocytes Isolated from Maternal Blood To demonstrate diagnostic utility of the present invention, a DNA probe set specific for a particular chromosome that provides both good signal to noise ratios and good spatial resolution of the fluorescent signals is used in in situ hybridization. Specific probe sets have been developed for five chromosomes frequently seen as liveborn aneuploidies, chromosomes 13, 18, 21, X and Y. A probe for chromosome 1 is used as a control. In constructing the probes, the general strategy was to identify a starting clone that mapped to the desired chromosomal region by multiple genetic and physical methods, and then to use that clone to identify matching cosmid "contigs" which are then used as hybridization probes. The chromosome 21 probe set is a three-cosmid contig containing 80 kb of nonoverlapping DNA. The chromosome 18 probe set is a three-cosmid contig containing 109 kb of nonoverlapping DNA. The chromosome 13 probe set is a three-cosmid contig containing approximately 97 kb of nonoverlapping DNA. The X chromosome probe is a cosmid containing a pericentromeric repeat sequence. The Y probe is pDP97, a repetitive clone (a 5.3 kb EcoRI Y fragment from cosmid Y97 subcloned into EcoRI site of pUC-13). All the probes are described in further detail in Klinger et al. *Am. J. Hum. Genet.* 51, 55–65 (1992).

To diagnose a chromosomal abnormality in a fetus, granulocytes are isolated from maternal blood as described in Example 1 and chromosomal abnormalities are assessed by performing in situ hybridization using chromosome-specific probes such as those described above. In situ hybridization is performed as described in Example 2 and in Klinger et al. *Am. J. Hum. Genet.* 51, 55–65 (1992) under suppression conditions (Cremer et al., Hum Genet 80:235–246 (1988); Lichter et al., Hum Genet 80:224–234 (1988)). Hybridization of the high copy number repeat sequences is suppressed by inclusion of total genomic human DNA, and the chromosomal specificity can be verified by hybridization to metaphase spreads. Probes are labelled with biotin-UTP, hybridized under suppression conditions, and specific hybridization detected by conjugated streptoavidin-FITC, which shows as a single "dot" in the FITC image upon microscopic analysis. Alternatively, if in situ hybridization is to be performed with multiple probes, the individual probes can be differentially labelled to allow for them to be distinguished fluorescently. For example, one probe can be labelled with biotin-UTP and the another with digoxigenin-UTP. The former probe can be detected with conjugated streptoavidin-FITC while the latter can be detected with conjugated anti-digoxigenin-Texas Red. The probes give sharp, punctate fluorescent signals in interphase cells that are easily discriminated and enumerated.

Diagnosis of a chromosomal abnormality is accomplished by comparing the hybridization of a chromosome-specific probe to DNA from fetal granulocytes to hybridization of the same probe to DNA from normal cells (a normal control). Normal cells, which may be any cells which do not contain a chromosomal abnormality in the chromosome(s) being examined, can be hybridized at the same time as the fetal granulocytes to provide a normal control. For example, maternal cells can be used as a normal control. Alternatively, a previously established normal control can be used for comparison. A common chromosomal abnormality, a trisomy (in which three copies of a particular chromosome are present in a cell rather that the normal two), can be diagnosed by detection of three fluorescent signals for a particular chromosome, e.g. commonly chromosomes 21, 18 or 13, in a fetal granulocyte as compared to only two fluorescent signals for the same chromosome in a normal control. A sufficient number of hybridized cells are examined to make a statistically significant determination of the number of fluorescent signals present per cell.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A non-invasive method for detecting the presence or absence of fetal nucleic acid in fetal granulocytes as a means for facilitating prenatal diagnosis of a chromosomal abnormality in a fetus, comprising:
   obtaining a sample of peripheral blood from a woman pregnant with a fetus;
   enriching for fetal granulocytes in a population of nucleated cells within the sample by increasing a proportion of fetal granulocytes in the population of nucleated cells relative to a proportion of fetal granulocytes in the population of nucleated cells prior to enrichment, thereby forming a sample enriched in fetal granulocytes; and
   performing in situ hybridization on the sample enriched in fetal granulocytes with a nucleic acid probe to generate resolved signals such that diagnosis of a chromosomal abnormality in the fetus is facilitated on the basis of the signals generated by detecting hybridization between the nucleic acid probe and nucleic acid from fetal granulocytes associated with the chromosomal abnormality.

2. The method of claim 1 wherein the sample enriched in fetal granulocytes is formed by separating non-nucleated cells from nucleated cells in the sample of peripheral blood forming a nucleated cell enriched sample and by treating the nucleated cell enriched sample such that a proportion of fetal granulocytes in the sample is increased relative to a proportion present in the nucleated cell enriched sample prior to enrichment forming a sample enriched in fetal granulocytes.

3. The method of claim 2 wherein the nucleated cell enriched sample is treated with at least one labelled monoclonal antibody which binds to fetal granulocytes but not to maternal cells and the sample enriched in fetal granulocytes is formed by separating cells which bind the labelled monoclonal antibody from the nucleated cell enriched sample.

4. The method of claim 2 wherein the nucleated cell enriched sample is treated with a labelled anti-CD71 monoclonal antibody and a labelled anti-glycophorin A antibody and the sample enriched in fetal granulocytes is formed by separating cells which bind the labelled anti-CD71 monoclonal antibody and the labelled anti-glycophorin A antibody from the nucleated cell enriched sample.

5. The method of claim 2 wherein the nucleated cell enriched sample is treated with a labelled anti-CD36 monoclonal antibody and a labelled anti-glycophorin A antibody and the sample enriched in fetal granulocytes is formed by separating cells which bind the labelled anti-CD36 monoclonal antibody and the labelled anti-glycophroin A antibody from the nucleated cell enriched sample.

6. The method of claim 1 wherein the chromosomal abnormality is a chromosomal ancuploidy.

7. The method of claim 6 wherein the chromosomal aneuploidy is trisomy 21.

8. The method of claim 6 wherein the chromosomal aneuploidy is trisomy 18.

9. The method of claim 6 wherein the chromosomal ancuploidy is trisomy 13.

10. The method of claim 2 wherein non-nucleated cells are separated from nucleated cells by density gradient centrifugation.

11. The method of claim 2 wherein non-nucleated cells are separated from nucleated cells by selective lysis of the non-nucleated cells.

12. The method of claim 1 wherein the in situ hybridization is fluorescent in situ hybridization.

13. The method of claim 1 wherein the nucleic acid from fetal granulocytes is Y chromosomal DNA.

14. The method of claim 1 wherein the nucleic acid from fetal granulocytes is associated with a disease.

15. The method of claim 14 wherein the disease is cystic fibrosis.

16. The method of claim 14 wherein the disease is Duchenne muscular dystrophy.

17. The method wherein the disease is hemophilia A.

18. The method of claim 14 wherein the disease is Gaucher disease.

19. The method of claim 14 wherein the disease is sickle cell anemia.

\* \* \* \* \*